United States Patent [19]

Jessup

[11] 4,402,684
[45] Sep. 6, 1983

[54] CANNULA WITH SOFT TIP

[75] Inventor: James L. Jessup, Elk Grove Village, Ill.

[73] Assignee: The Kendall Company, Boston, Mass.

[21] Appl. No.: 302,875

[22] Filed: Sep. 16, 1981

[51] Int. Cl.³ .................... A61M 19/00; A61M 25/00; A61M 31/00

[52] U.S. Cl. ..................................... 604/264; 604/43; 604/54; 604/282; 128/200.22; 128/207.14

[58] Field of Search ................. 128/348, 349 R, 250, 128/251, 248, 200.26, 200.14, 207.14, 239, 240, 241, 350 R, 200.22; 604/282, 43, 170, 264, 280, 281, 54

[56] References Cited

U.S. PATENT DOCUMENTS

| | | | |
|---|---|---|---|
| 2,135,052 | 11/1938 | Rose | 128/250 |
| 3,154,075 | 10/1964 | Weckesser | 128/251 |
| 3,512,526 | 5/1970 | Fielding | 128/251 |
| 3,630,206 | 12/1971 | Gingold | 128/240 X |
| 3,885,567 | 5/1975 | Ross | 128/240 X |
| 3,957,055 | 5/1976 | Linder et al. | 128/200.26 |
| 4,068,664 | 1/1978 | Sharp et al. | 128/240 X |
| 4,167,186 | 9/1979 | Pick et al. | 128/251 |
| 4,239,042 | 12/1980 | Asai | 128/348 |

FOREIGN PATENT DOCUMENTS 105038  3/1917  United Kingdom ............ 128/350 R

Primary Examiner—Richard J. Apley
Assistant Examiner—Michelle N. Lester
Attorney, Agent, or Firm—Powell L. Sprunger

[57] ABSTRACT

A cannula comprising, an elongated catheter of elastic material and having a relatively soft distal tip. The catheter has a lumen extending from the tip to a proximal end of the catheter, and a plurality of openings in a distal end portion of the catheter communicating between the lumen and the outside of the catheter. The cannula has an elongated relatively rigid stylet snugly received in the catheter lumen, with the cannula having one or more channels communicating between a proximal end of the stylet and the openings.

2 Claims, 5 Drawing Figures

CANNULA WITH SOFT TIP

BACKGROUND OF THE INVENTION

The present invention relates to cannulas.

It is a common procedure to spray the laryngotracheal area with a topical anesthetic prior to endotracheal intubation, but the present catheters to accomplish this result are deficient. It is desirable for such catheters to have a soft tip to prevent perforating the trachea and damage to the vocal cords during use. It is also desirable for the catheters to have a curve in the distal end portion of the catheters to fit the trachea. However, if the catheters are made from a soft material to provide the soft tip, the catheters are too flexible and do not maintain the desired curve.

SUMMARY OF THE INVENTION

A principal feature of the invention is the provision of an improved cannula.

The cannula of the present invention comprises, an elongated catheter of elastic material and having a distal tip, a lumen extending from the tip to a proximal end of the catheter, and a plurality of openings in a distal end portion of the catheter communicating between the lumen and the outside of the catheter. The cannula has an elongated relatively rigid stylet snugly received in the catheter lumen, with the catheter and stylet defining channel means communicating between a proximal end of the stylet and the openings.

A feature of the present invention is that the tip of a syringe may be attached to the proximal end of the catheter in order to pump a topical anesthetic into the channel means.

Another feature of the invention is that the cannula sprays the topical anesthetic through the catheter openings onto the laryngotracheal area.

A further feature of the invention is that the catheter tip is relatively soft to prevent perforating the trachea and damage to the vocal chords during use of the cannula.

Yet another feature of the invention is that the stylet has a curved distal end portion to impart a curve to the cannula in order to fit the trachea.

Thus, a feature of the present invention is that the cannula has a relatively soft tip and a curve in the distal end portion of the cannula.

Further features will become more fully apparent in the following description of the embodiments of this invention and from the appended claims.

DESCRIPTION OF THE PREFERRED EMBODIMENTS

Figure 1:
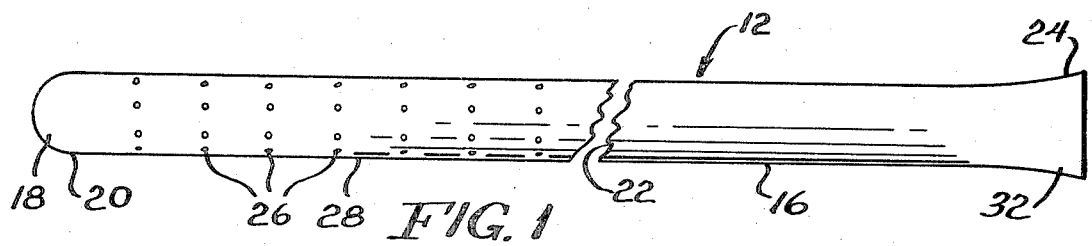
FIG. 1 is a fragmentary elevational view of a catheter for a cannula of the present invention.
Figure 2:
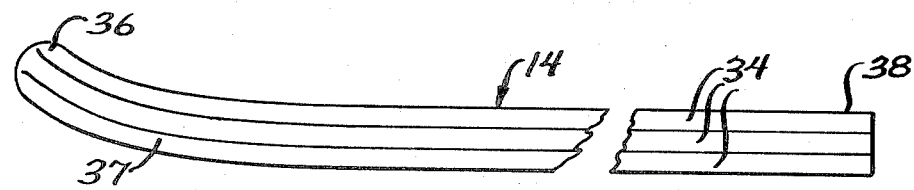
FIG. 2 is a fragmentary elevational view of a stylet for the catheter of FIG. 1.
Figure 3:
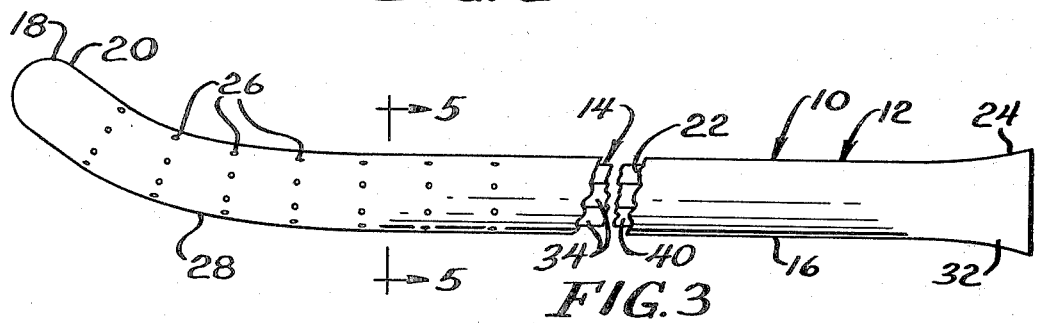
FIG. 3 is a fragmentary elevational view of the cannula of the present invention.
Figure 4:
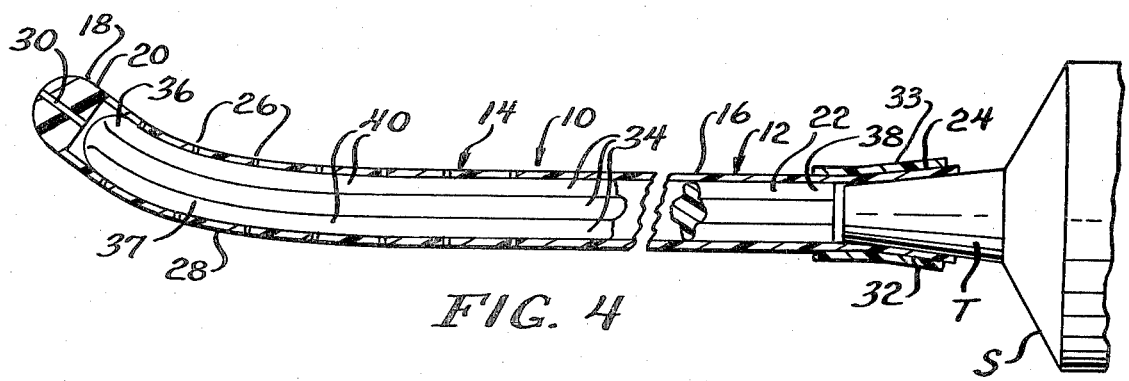
FIG. 4 is a fragmentary sectional view of the cannula of FIG. 3.
Figure 5:
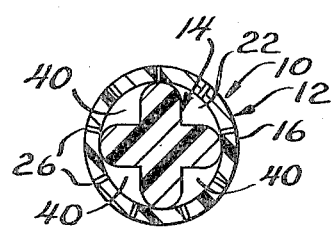
FIG. 5 is a sectional view taken substantially as indicated along the line 5—5 of FIG. 3.

Referring now to FIGS. 1-5, there is shown an elongated cannula generally designated 10 having an outer catheter 12 and an inner stylet 14. The catheter 12 has a generally cylindrical wall 16, and a tip 18 at a distal end 20 of the catheter 12, with the wall 16 defining a lumen 22 of the catheter 12 extending from the tip 18 to a proximal end 24 of the catheter 12. As shown, the catheter 12 has a plurality of relatively small openings 26 extending through the wall 16 of the catheter 12 in a distal end portion 28 of the catheter 12, with the openings 26 communicating between the lumen 22 and the outside of the catheter 12. Also, in a preferred form, the tip 18 has an opening 30 extending through the tip 18 to the lumen 22. The proximal end 24 of the catheter 12 has a taper 32 in order to receive the tip T of a syringe S with the taper 32 sealingly engaging against the tip T. The taper 32 may have an outer sleeve 33 for purposes of rigidity. The catheter 12 may be made of a suitable soft elastic material, such as silicone rubber, in order to provide the catheter 12 with a relatively soft tip 18.

The stylet 14 is made from a relatively rigid material, such as polypropylene or nylon. The stylet 14 has four elongated spaced ribs 34 extending outwardly from the stylet 14. As shown, the stylet 14 is snugly received in the lumen 22 of the catheter 12 with a distal end 36 of the stylet 14 located adjacent the tip 18 of the catheter 12, and with a proximal end 38 of the stylet 14 being recessed from the taper 32 at the proximal end 24 of the catheter 12. The ribs 34 of the stylet 14 define four spaced channels 40 intermediate the stylet 14 and the catheter 12, with the channels 40 communicating between the proximal end 38 of the stylet 14 to the openings 26 and 30 of the catheter 12. The stylet 14 has a curve in a distal end portion 37 of the stylet 14, such that the relatively rigid stylet 14 imparts a curve to the cannula 10.

In use, the tip T of the syringe S is attached to the taper 32 of the catheter 12, and the syringe S is pumped in order to eject a topical anesthetic from the syringe S through the channels 40 and openings 26 and 30 onto the laryngotracheal area of the patient. During insertion of the cannula 10, the relatively soft tip 18 prevents perforation of the trachea and damage to the vocal chords of the patient. Also, the curve in the distal end portion 37 of the stylet 14 imparts a curve in the distal end portion 28 of the catheter 12 in order to fit the trachea. Thus, the cannula 10 has a relatively soft tip 18 even though the cannula 10 has sufficient rigidity to maintain the curve in the distal end portion 28 of the catheter 12. Also, the stylet 14 imparts sufficient stiffness to the cannula 10 to permit lifting of the epiglottis during insertion of the cannula 10.

The foregoing detailed description is given for clearness of understanding only, and no unnecessary limitations should be understood therefrom, as modifications will be obvious to those skilled in the art.

I claim:

1. A cannula for application of a topical anesthetic to the laryngotracheal area of a patient prior to an endotracheal intubation procedure, comprising: an elongated catheter of soft, elastic material and having an integral, relatively soft distal tip, an integral proximal end, a lumen extending from the tip to the proximal end of the catheter, and means defining a plurality of openings in a distal end portion of the catheter communicating between the lumen and the outside of the catheter; and an elongated, rigid, shape-retaining, solid stylet snugly interfitted within the catheter lumen and extending substantially but somewhat less than the full length of the catheter, the distal end portion of the stylet being permanently curved, the stylet distal end portion being spaced from the distal tip of the catheter, the stylet having an X configuration in cross section, the webs of the X configured stylet being of substantial thickness with respect to the diameter of the stylet, the outer peripheries of the webs being curved so as to snugly interfit with and permanently engage the inner wall of the catheter, thus to define a plurality of fluid passageways between the stylet and the catheter, said rigid stylet engaging against and being permanently retained within the catheter, the stylet having a proximal end which is recessed from the proximal end of the catheter, the proximal end of the catheter being configured to receive a syringe tip, whereby, when the cannula is assembled with a syringe tip, the stylet proximal end is spaced from the syringe tip, and whereby, in use, the cannula may be inserted into the laryngotracheal area of a patient without trauma, due to the elastic structure of the catheter, and a topical anesthetic may be applied in the laryngotracheal area, the anesthetic passing from a syringe connected to the proximal end of the catheter, through the passageways defined by the stylet channels and the catheter, to and through the openings in the distal end portion of the catheter, and thus to the laryngotracheal area of a patient.

2. The cannula of claim 1 including an opening extending through the catheter tip.

* * * * *